United States Patent [19]

Mann

[11] Patent Number: 5,151,027
[45] Date of Patent: Sep. 29, 1992

[54] ORTHODONTIC DEVICE FOR SMALL ANIMALS

[76] Inventor: Lloyd J. Mann, 150 South Rossevelt, #3008, Mesa, Ariz. 85202

[21] Appl. No.: 408,774

[22] Filed: Sep. 18, 1989

[51] Int. Cl.⁵ .............................................. A61D 5/00
[52] U.S. Cl. ....................................................... 433/1
[58] Field of Search ...................... 433/1, 6, 18, 19, 24, 433/2

[56] References Cited

U.S. PATENT DOCUMENTS

| | | | |
|---|---|---|---|
| 1,597,529 | 8/1926 | Leonard | 433/19 |
| 3,034,215 | 5/1962 | Doster | 433/18 |
| 3,140,543 | 7/1964 | Menter | 433/1 |
| 3,416,228 | 12/1968 | Grimmett | 433/19 |
| 3,454,001 | 7/1969 | Stockfisch | 433/6 X |
| 3,820,242 | 6/1974 | Haskins | 433/18 |
| 3,837,081 | 9/1974 | Kesling | 433/6 |
| 3,967,379 | 7/1976 | Bergersen | 433/24 X |
| 4,468,196 | 8/1984 | Veller | 433/24 |
| 4,480,994 | 11/1984 | Hoffman | 433/6 |
| 4,573,914 | 3/1986 | Nord | 433/18 |
| 4,676,745 | 6/1987 | Zurita | 433/6 |
| 4,802,849 | 2/1989 | Collins, Jr. | 433/18 X |
| 4,830,612 | 5/1989 | Bergersen | 433/24 X |
| 4,840,562 | 6/1989 | Wilson et al. | 433/23 |
| 4,950,158 | 8/1990 | Barngrover et al. | 433/18 X |

FOREIGN PATENT DOCUMENTS

| | | | |
|---|---|---|---|
| 597682 | 9/1959 | Italy | 433/18 |
| 1149964 | 4/1985 | U.S.S.R. | 433/19 |
| 1250284 | 8/1986 | U.S.S.R. | 433/2 |

*Primary Examiner*—Robert P. Swiatek
*Assistant Examiner*—Nicholes D. Luccheri
*Attorney, Agent, or Firm*—James F. Duffy

[57] ABSTRACT

A veterinary orthodontic fixture useful in correcting lingual displacement of the mandibular canine teeth of an animal. When the fixture is in place, inclined biting planes coupled to the maxillary cannies cause a buccal displacement of the mandibular cannies so as to move the mandibular cannies into their normal position where they will not traumatically interfere with the gingival tissue of the maxilla. A telescoping rod bridging the fixture from one canine tooth to the other provides a torque resistent element which prevents undue stress from being exerted on the maxillary canine onto which the fixture is attached. Because this rod is telescoping, no inhibiting restraints are placed on the normal growth development of the animal's jaw while the fixture is in place.

12 Claims, 2 Drawing Sheets

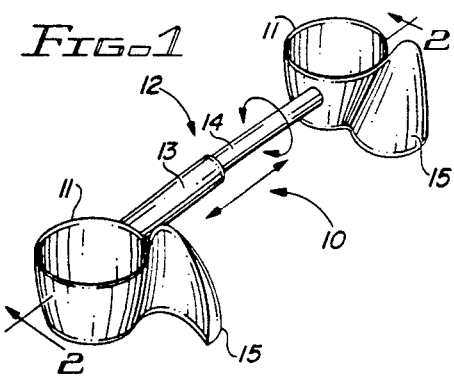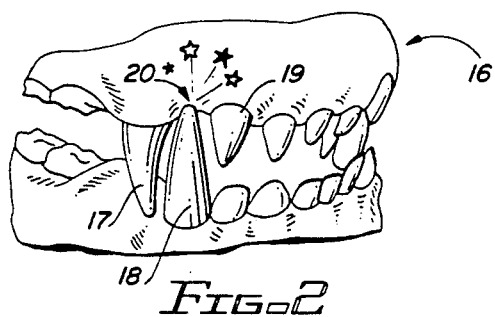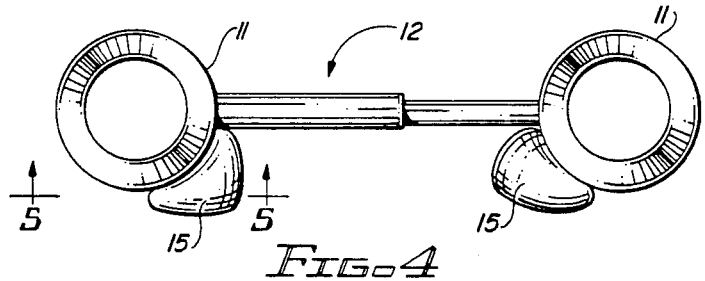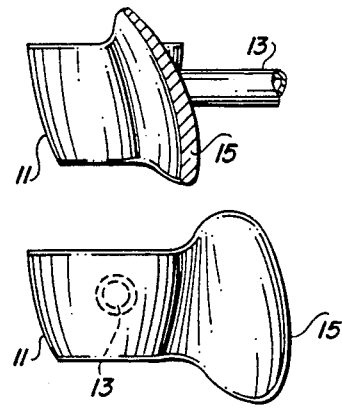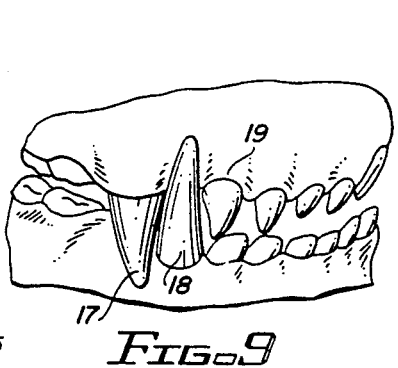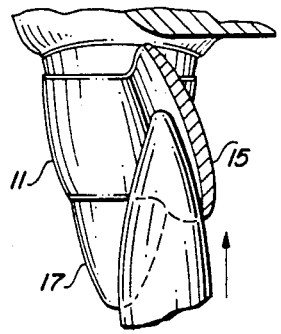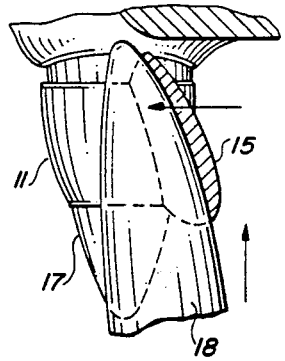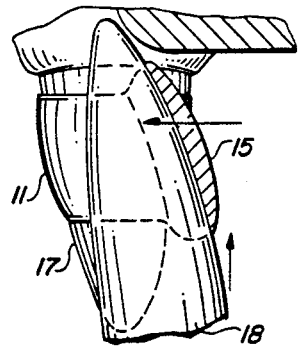

ORTHODONTIC DEVICE FOR SMALL ANIMALS

BACKGROUND

1. Field of the Invention

The invention relates to veterinary dentistry. In particular, the invention relates to an orthodontic device to be used in correcting the "base narrow" condition which often occurs following retention of deciduous canine teeth.

2. Prior Art

Lingual displacement of mandibular canine teeth often occurs following retention of deciduous canine teeth. This "base narrow" condition often results in trauma of occlusion to the lingual aspect of the maxillary canine teeth resulting in the development of a periodontal pocket or an oronasal fistula. In other words, if a small animal, for example, a puppy, retains his first or, puppy, teeth after its second, or adult, canines have erupted from the gums, the lower, or mandibular, canines may incline inwardly to the extent wherein they come in contact with the gums and fleshy portions of the upper part of the mouth.

The situation may be stated more precisely as follows: retention of deciduous canine teeth may lead to lingual displacement of the permanent canine teeth. The coronal aspect of the mandibular canine teeth can result in the trauma of occlusion to the palate on the lingual aspect of the maxillary canine teeth. This, in turn, results in the development of a periodontal pocket; an oronasal fistula which can result in a life threatening episode for the animal.

Lingual displacements of the canine teeth of the lower jaw are corrected by emplacing a palatal plate in a position such that the displaced canine teeth strike the plate. These plates are frequently referred to as bit plates or bite planes. Such bite planes may be fixed or removable and may be constructed of acrylic or of metal.

Prior art procedures require frequent examination and possible replacement of the bite planes during the course of treatment. The bite planes must be allowed to produce no restraint on the normal growth of the jaw as the puppy or other small animal advances in age. Bite planes made from acrylic should be removable for cleaning. Fixed acrylic bite planes often cause significant irritation as a result of food entrapment and stomatitis if the bite planes are not kept properly clean.

It is an objective of the invention to provide a non-irritating bite plane which requires minimum cleaning procedures and which may remain in place in the animal's mouth during the entire course of treatment.

SUMMARY OF THE INVENTION

The invention is an orthodontic fixture intended for use with animals to correct lingually displaced canine teeth. A bite plane is emplaced within the animal's mouth to make interfering contact with a displaced mandibular canine tooth. This repeated interfering contact between tooth and bite plate moves the tooth buccally into its proper functioning position within the animal's mouth. To maintain the bite plane in position, tooth coupling means are employed.

Disclosed and claimed is a torque resisting means which is then coupled to the tooth coupling means. The torque resisting means resists the stress tipping moments which are generated when interfering contact is made between a displaced mandibular canine tooth and the bite plane. By resisting these stress moments, movement of the tooth to which the bite plane is coupled is restrained.

In general the tooth coupling means provides means for encircling a maxillary tooth. This encircling means preferably comprises a coupling band which encompasses a maxillary canine tooth. The coupling band is maintained in position by cementing the band to the canine tooth. The torque resisting means then consists of a rod coupled to the coupling band and extending lingually from the coupling band into the mouth of the animal into which the fixture is emplaced. The distal end of the rod is fixedly positioned within the mouth of the animal. Disclosed and claimed are means for adjustably and selectedly sizing the tooth coupling band as may be required to enable the band to properly encompass a selected canine tooth of an animal. Means are also provided for latching the band to maintain it at a selected size.

The bite plane may be fixedly coupled to the tooth coupling band or, in an alternate embodiment, adjustably and releasedly coupled to the tooth coupling band.

Since the lingual displacement of mandibular canine teeth usually affects both canines, on either side of the animal's jaw, the orthodontic fixture is disclosed as comprising tooth coupling means on both sides of the animal's jaw. Each of these tooth coupling means has a bite plane coupled thereto. The torque resistent rod connects the tooth coupling means at either side of the jaw of the animal in which the fixture is emplaced. Because the lingually displaced canine problem usually arises in young animals, the torque resistent rod is a telescoping rod which automatically adjusts in length as the jaw of the animal increases with the animal's age. The fixture thus places no restriction on the growth of the young animal's jaw.

DESCRIPTION OF THE DRAWINGS

FIG. 1 illustrates the orthodontic fixture of the invention showing a pair of mandibular canine tooth coupling bands each with an inclined biting plane coupled thereto. The bands are joined by a freely telescoping rod so as to permit normal growth of the animal's jaw while the fixture is in place.

FIG. 2 illustrates the result of the lingual displacement of the mandibular canines resulting in traumatic contact by those canines with the gingival tissue along the upper gum line.

FIG. 3 is a cross sectional view of the invention taken along line 2—2 of FIG. 1.

FIG. 4 is a bottom plan view of the illustration of the invention shown in FIG. 1.

FIG. 5 is view taken along the lines 5—5 of FIG. 4.

FIG. 6 is an elevation view taken from the left side of the illustration of FIG. 5.

FIGS. 8A-8C illustrate, in sequence, the tipping of the mandibular canine teeth produced, over a period of time, by contact of the teeth with the biting plane of the fixture.

FIG. 9 illustrates the correction in the displacement of the mandibular canine tooth to produce a normal non-traumatic relationship of the tooth with the gingival tissue of the upper jaw.

FIG. 10 is a plan view of an adjustable tooth coupling band having a replaceable and adjustable bite plane attached thereto.

FIG. 11 is an elevation view taken along the lines 11—11 of FIG. 10.

FIG. 12 is an elevation view of the fixture taken from the left of the figure illustrated in FIG. 11.

FIG. 13 is an exploded, partial sectional view of the assembly of the biting plane to the tooth coupling band. The illustrated combination of coupling elements permits the biting plane to be moved through a variety of adjustment positions as may be required to accomodate the mouth conditions of a given animal patient.

A DETAILED DESCRIPTION OF THE INVENTION

Figure 7:
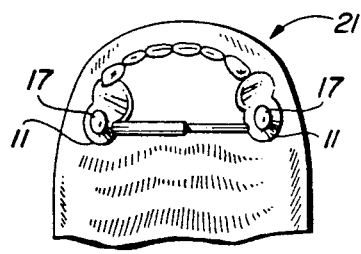
FIG. 7 is a view of the upper jaw of the animal with the invention in place.

For purposes of promoting an understanding of the principles of the invention, reference will now be made to the embodiments illustrated in the drawings and specific language will be used to describe same. It will nevertheless be understood that no limitation of the scope of the invention is thereby intended, there being contemplated such alterations and modifications of the illustrated device, and such further applications of the principles of the invention as disclosed herein, as would normally occur to one skilled in the art to which the invention pertains.

The orthodontic fixture disclosed and claimed herein is intended for use with any animal which may be benefited by utilizing the fixture. For purposes of exposition a small animal, in particular, a puppy or a young dog, will be referred to. Such reference is not intended to limit the use of the invention.

The invention 10 is an orthodontic device useful in correcting the lingual displacement of mandibular canine teeth in a young dog, or other animal, resulting from retention of the deciduous canine teeth. The resultant condition, known as "base narrow" condition results in trauma to the maxillary gingival tissue in a manner illustrated in FIG. 2. In the illustration of FIG. 2 the mandibular canine 18 is emplaced normally between maxillary canine 17 and maxillary incisor 19. However, due to the lingual displacement of canine 18, the tip of canine 18 strikes the gingival tissue at 20. Repeated contact with the gingival tissue is traumatic and can result in an oronasal fistula.

In treating the condition illustrated in FIG. 2, the veterinary orthodontist makes impressions of the anterior dental arcades. These impressions are utilized to make plaster molds from the study of which a fixed inclined bite plane is designed for the particular animal patient. The use of non-allergenic metal for the bite planes is recommended since acrylic bite planes often cause ulceration and inflammation when formed, in-place, in the animal's mouth and when food entrapment and stomatitis results from improper cleaning.

As will be disclosed, the invention 10, FIG. 1, is preferably made of non-allergenic metal and is incorporated into the patient's mouth in a manner which makes for easy cleaning. Further, the corrective buccal displacement of the mandibular canine's occurs in a relatively short span of time such that potential complications experienced in the prior art are avoided.

In FIG. 1, the invention 10 is seen to comprise a pair of tooth coupling bands 11. Bands 11 are in turn coupled by telescoping rod 12 comprised of an exterior cylinder 13 and slide rod 14 which is free to slide and rotate within cylinder 13. Thus, tooth coupling bands 11 may be rotatingly displaced in their angular disposition as well as longitudinally displaced one from the other. To each coupling band 11 an inclined biting plane 15 is attached.

Illustrations of the invention in FIGS. 4–6 show clearly the manner in which the bite planes 15 are affixed to tooth coupling bands 11. FIG. 5 in particular illustrates the incline of the bit plane 15. The tooth to be corrected, the mandibular canine 18, would move upward against the biting plane of FIG. 5 and be caused to be directed outward and to the right of the illustration of FIG. 5. This causes the tooth to be displaced outward toward the cheek (buccal movement) such that the traumatic contact of the mandibular canine 18 with the gingival tissue of the animal's mouth 16 at point 20 will be avoided.

In use, the invention 10 is fixed in place by coupling bands 11 to maxillary canines 17 in the manner illustrated in FIG. 7. FIG. 7 is a view of the roof 21 of the animal's mouth. With tooth coupling bands 11 cemented to canines 17, telescoping rod 12 bridges the separation spanning canines 17.

In FIG. 8A, the interaction of the mandibular canine 18 with inclined plate 15 is shown. In this and the illustrations 8B and 8C, coupling band 11 has been cemented to maxillary canine 17. When the animal closes its mouth, mandibular canine 18 moves upward into intimate contact with inclined plate 15. In the illustration of FIG. 8A, the situation is that experienced immediately after installation of the orthodontic fixture 10, the invention, within the animal's mouth. The animal is incapable of fully closing its mouth because of the lingual displacement of the mandibular canines. Over a period of time, the mandibular canines will be displaced buccal, that is, outwardly toward the cheeks of the animal. This condition is illustrated in FIG. 8B at an intermediate point in the treatment. The animal may close its mouth further than it could at the start of the treatment, FIG. 8A, but cannot yet fully close its mouth.

At, or near the end of the treatment, the situation illustrated in FIG. 8C exists. The animal may fully close its mouth and there is no traumatic contact of mandibular canine 18 with the gingival tissue of the mouth. In a 6-month old dog, the corrective displacement of the mandibular canine teeth may be achieved in as little as 5 days. A 10-month old dog may require approximately 10 days to move the lingually displaced mandibular canine teeth. Older dogs may require 3 to 6 weeks and sometimes longer to achieve correction of the condition.

While the times in which the orthodontic fixtures emplaced within the animal's mouth seem relatively short, it must be remembered that significant growth of the animal takes place in such short periods of time at that period of the animal's life. Thus, it is necessary that there be no restriction on the growth of the jaw while the fixture is in place. The maxilla will experience significant growth in width and length during this period of time. Telescoping bar 12 in its ability to allow the continued expansion of growth of the maxilla imposes no restriction on this growth. As the skull expands in width, so too, does the appliance 10. While telescoping rod 12 permits for the continued growth of the skull, it also serves a significant mechanical advantage in resisting any moments of force generated by the contact between the mandibular canines 18 and the inclined bite plates 15.

In certain animals, the mandibular canine teeth will be displaced not only lingually but also distally. To correct these conditions simultaneously, the bite plane 15 must be modified so as to cause a corrective displacement of the maxillary canines 18 in both a mesial as well as a buccal direction. To accomplish this, a groove, not shown, is impressed into each bite plane so as to tip the tooth in one corrective motion into its normal position.

All mouth actions of the animal cooperate to achieve the corrective displacement of the mandibular canines into their proper position. Each opening and closing of the dog's mouth acts to direct the canine to its proper position. A dog sleeping with its mouth closed, as is typical, is unconsciously assisting in the corrective displacement of its canine teeth to their proper position.

In the embodiment of the invention just disclosed the coupling bands 11 and the bite planes 15 were fabricated after a study of a plaster model fabricated from impressions made on the animal's mouth. To provide orthodontic dentists with a greater latitude in preparing orthodontic devices which are the functional equivalent of the embodiment of the invention just described, a second embodiment of the invention will now be disclosed. In this second embodiment, the canine tooth coupling bands, now having a reference 31, are adjustable so as to be adaptable for use on canine teeth falling within a selected range of tooth sizes. Similarly, the inclined bite plane, now referred to as 35, is removably and adjustably coupled to tooth band 31. The ability to select and assemble coupling bands 31 and inclined planes 35 from a stock of these items of various sizes will enable an orthodontic veterinarian to assemble an orthodontic fixture which may be readily utilized with a particular animal patient without the need to make impressions and molds.

Figure 10:
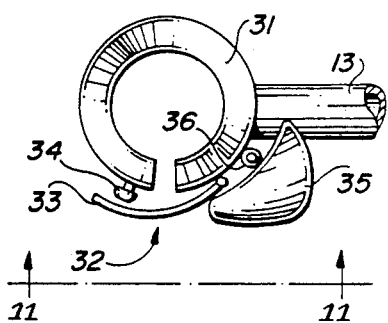

The illustration of FIG. 10 is similar to that of FIG. 4, the first embodiment. Tooth coupling band 31 is provided with sizing and latching means 32. Means 32 are illustrated also in FIGS. 11 and 12 (analogous to FIGS. 5 and 6). Sizing and latching means 32 is seen to comprise a strap 33 having a plurality of holes 37 therein. Holes 37 accommodate latching post 34. By positioning latching post 34 within the proper hole 37, band 31 may be made to fit a canine tooth snugly enough to be cemented in place on the tooth.

Figure 11:
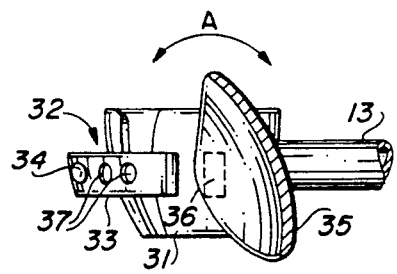
FIGS. 10-13 illustrate a second embodiment of the invention in which the inclined bite plane is replaceable and adjustable once coupled to the tooth retaining bands. In this embodiment, the band is adjustable for coupling to maxillary canines of various diameters.
Figure 12:
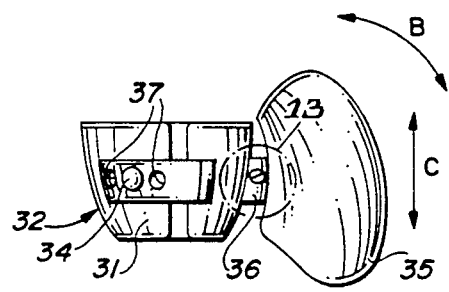

FIGS. 10–12 also illustrate the means 36 for adjustably and removably coupling inclined plate 35 to tooth coupling band 31. The Arrow A in FIG. 11 indicates that the angular disposition of inclined plate 35 from the vertical may be adjusted by means of removable, adjustable coupling means 36.

In FIG. 12, Arrow B indicates that inclined plane 35 may be rotatably adjusted within the plane of the illustration to the extent permitted by means 36. Arrow C indicates that inclined plane C may be lineally adjusted upward or downward with respect to coupling band 31 as set forth in the illustration of FIG. 12.

Figure 13:
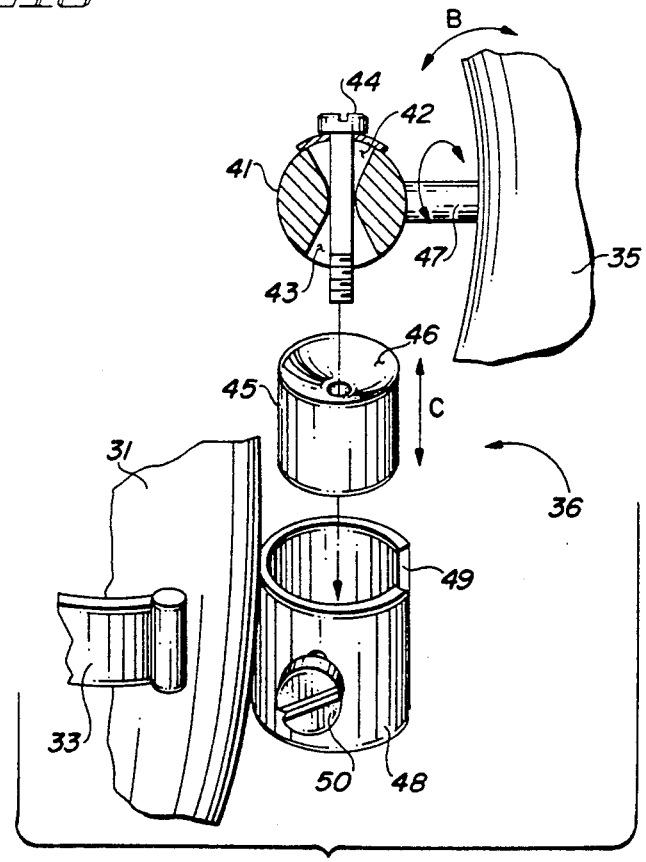

Details of removable and adjustable coupling means 36 are set out in the exploded assembly drawing of FIG. 13. Bite plane 35 of FIG. 13 represents one of a plurality of bite planes of varying sizes and configurations maintained by the orthodontist to be selected and assembled to a selected one of a variety of tooth coupling bands 31. The selection of bands 31 and plates 35 is in accord with the dimensions and characteristics of the teeth and gingival tissue of the particular animal patient being treated at the moment.

Plate 35 is coupled by means of rod 47 to sphere 41. Those skilled in the dental arts will recognize sphere 41 as a coupling device with internal characteristics which permit it to be coupled in various dispositions within the concavity 46 of slide rod 45.

Sphere 41 is illustrated in section in FIG. 13. Sphere 41 contains two voids, 42 and 43. Voids 42 and 43 are circularly cylindrical in shape with the apex of each circular cylindrical void overlapping at the central area region of sphere 41. When a screw fastener 44 is inserted into void 42 and exits from void 43, sphere 41 may be rotated about screw fastener 44 to an extent limited only by the size of voids 42 and 43.

The configuration of voids 42 and 43 within sphere 41 permits limited rotation of bite plane 35 in and out of the paper on which FIG. 3 is illustrated, as indicated by Arrow A and within the plane of the paper as indicated by Arrow B.

Screw fastener 44 couples sphere 41 to slide rod 45. With sphere 41 emplaced within concavity 46 and adjusted to the particular angular disposition that the dentist requires, screw fastener 44 may be tightened to lock bite plane 35 into that desired disposition with respect to slide rod 45. Slide rod 45 is positioned downward within slotted cylinder 48. Slide rod 45 may be lockingly positioned within slotted cylinder 48 by means of screw fastener 50. One or more such screw fasteners 50 may be employed to permit slide rod 45 to be positioned anywhere within the confines of slotted cylinder 48. Screw fastener 50 is adjusted to bear on the surface of slide rod 45 and thus maintain it in its position within slotted cylinder 48. Slot 49, within cylinder 48, provides free passage of coupling rod 47 which couples bite plane 35 to sphere 41.

Slotted cylinder 48 is mechanically coupled to tooth coupling band 31. Each of the plurality of varying size bands 31 maintained by the dentist will preferably comprise the assembly of slotted cylinder 48 and coupling band 31.

To utilize the second embodiment of the invention, coupling band 31 is selected to fit the maxillary canine of the animal being treated. The adjustable locking and latching means 32 is employed to properly size band 31 to be cemented onto the canine tooth of the animal patient. A bite plane 35 of the shape and size suitable for use in correcting the mandibular canine tooth displacement of the animal patient is selected from the store of bite planes maintained by the dentist. Screw fastener 44 maintains a loose coupling between sphere 41 and slide rod 45 so that the angular disposition of bite plane 35 may be adjusted. Slide rod 45 is then positioned downward within slotted cylinder 48 and the height and angular dispositon of bite plane 35 is established for the particular patient. Locking screws 50 and 44 are then set to maintain the relationship desired among coupling band 31, bite plane 35, and the teeth and gums of the animal patient. Band 31 is cemented to the maxillary canine to maintain the device in position.

Embodiment two may readily make use of the telescoping rod 12 disclosed with respect to the first embodiment of the invention. As already noted, rod 12 provides a torque resisting element which prevents excessive moment forces being applied to the maxillary canines to which coupling band 31 is cemented. Further, the telescoping characteristics of rod 12 permit the animal's jaw to grow in a normal manner while the fixture is in place.

What has been disclosed is a veterinary orthodontic fixture useful in correcting lingual displacement of the mandibular canine teeth of an animal. When the fixture is in place, inclined biting planes coupled to the maxillary canines cause a buccal displacement of the mandibular canines so as to move the mandibular canines into their normal position where they will not traumatically interfere with the gingival tissue of the maxilla. A telescoping rod bridging the fixture from one canine tooth to the other provides a torque resistent element which prevents undue stress from being exerted on the maxillary canine onto which the fixture is attached. Because this rod is telescoping, no inhibiting restraints are placed on the normal growth development of the animal's jaw while the fixture is in place.

Those skilled in the art will conceive of other embodiments of the invention which may be drawn from the disclosure herein. To the extent that such other embodiments are so drawn, it is intended that they shall fall within the ambit of protection provided by the claims herein.

Having described the invention in the foregoing description and drawings in such a clear and concise manner that those skilled in the art may readily understand and practice the invention, That Which is Claimed is:

1. An animal orthodontic fixture for the correction of displaced mandibular canine teeth comprising:
   a bite plane for emplacement within an animal's mouth to make interfering contact with a displaced mandibular canine tooth of an animal for bucally moving said mandibular canine tooth to its proper functioning position within an animal's mouth;
   tooth coupling means coupled to said bite plane, for coupling said bite plane in position within an animal's mouth to make interfering contact between said bite plane and a displaced mandibular canine tooth of an animal;
   torque resisting means coupled to said tooth coupling means for resisting stress moments generated by interfering contact made between a displaced mandibular canine tooth and said bite plane;
   a second said bite plane and a second said tooth coupling means; and
   said torque resisting means comprises a rod connecting said tooth coupling means to said second tooth coupling means, said rod extending lingually from each said tooth coupling means within the mouth of an animal in which said fixture is emplaced.

2. The fixture of claim 1, wherein said tooth coupling means comprises means for encompassing a maxillary tooth of an animal.

3. The fixture of claim 2 wherein each said means for encompassing a maxillary tooth comprises a coupling band for encompasing a maxillary canine tooth of an animal.

4. The fixture of claim 3 wherein said coupling band further comprises adjustment means for selectedly sizing said band to encompass a selected maxillary canine tooth of an animal and for latching said band to a selected size.

5. The fixture of claim 1 wherein said rod is a telescoping rod, self adjustable in length as the jaw of a growing animal, wearing said fixture, increases in size with age of the animal.

6. The fixture of claim 5 wherein each said tooth coupling means comprises a coupling band for encompassing a maxillary canine tooth of an animal.

7. The fixture of claim 6 wherein said coupling band comprises adjustment means for selectedly sizing said band to encompass a selected maxillary canine tooth of an animal and for latching said band to a selected size.

8. The fixture of claim 1 wherein each said tooth coupling means comprises a coupling band for encompassing a maxillary canine tooth of an animal.

9. The fixture of claim 8 wherein said coupling band further comprises adjustment means for selectedly sizing said band to encompass a selected maxillary canine tooth of an animal and for latching said band to a selected size.

10. The fixture of claim 1 further comprising bite plane coupling means for releasedly and adjustably coupling each said bite plane to each said tooth coupling means.

11. The fixture of claim 10 wherein each said tooth coupling means comprises a coupling band for encompassing a maxillary canine tooth of an animal.

12. The fixture of claim 11 wherein said coupling band further comprises adjustment means for selectedly sizing said band to encompass a selected maxillary canine tooth of an animal and for latching said band to a selected size.

* * * * *